United States Patent [19]

Khalid

[11] Patent Number: 5,776,189
[45] Date of Patent: Jul. 7, 1998

[54] CARDIAC VALVULAR SUPPORT PROSTHESIS

[76] Inventor: Naqeeb Khalid, 764/N Samanabad, Lahore, Pakistan

[21] Appl. No.: 811,211
[22] Filed: Mar. 5, 1997
[51] Int. Cl.⁶ ........................................................ A61F 2/24
[52] U.S. Cl. .............................................................. 623/2
[58] Field of Search ................................................. 623/2

[56] References Cited

U.S. PATENT DOCUMENTS

| | | |
|---|---|---|
| 3,656,185 | 4/1972 | Carpentier . |
| 4,055,861 | 11/1977 | Carpentier et al. . |
| 5,607,471 | 3/1997 | Seguin et al. ........................ 623/2 |

FOREIGN PATENT DOCUMENTS

| | | |
|---|---|---|
| 257874 | 3/1988 | European Pat. Off. . |
| 595791 | 5/1994 | European Pat. Off. . |
| 9315690 | 8/1993 | WIPO . |
| 9503757 | 2/1995 | WIPO . |

OTHER PUBLICATIONS

C.-H. Chang et al., Annals of Thoracic Surgery, vol. 57, Issue 3, pp. 644–647 (1994).

*Primary Examiner*—David H. Willse
*Attorney, Agent, or Firm*—Foley & Lardner

[57] ABSTRACT

The invention is concerned with a support prosthesis for a natural human heart valve having an annulus of generally oval configuration with a major axis and a minor axis and at least two leaflets stemming from the annulus and each moving along a naturally preordained path during systolic contraction or diastolic expansion. The support prosthesis according to the invention consists of an oblong, annular flexible member of a size and shape to fit against the annulus, the member having a longitudinal axis and being made of a biocompatible material exhibiting elasticity only along the longitudinal axis so as to permit dilatation of the annulus along the major axis thereof, in response to heamodynamic and functional changes, while preventing dilatation of said annulus along the minor axis thereof so that the path along which each said leaflet travels remains unaltered. Because of its pliable nature, the support prosthesis of the invention does not produce a systolic anterior motion of the mitral valve. The use of such a support prosthesis prevents dilatation of the annulus along its minor axis and thereby prevents nonclosure of the mitral and tricuspid valves during systolic contraction. During diastolic expansion, the annulus can dilate along its major axis in response to the increased blood flow and pressure in different physiological and pathological states.

10 Claims, 2 Drawing Sheets

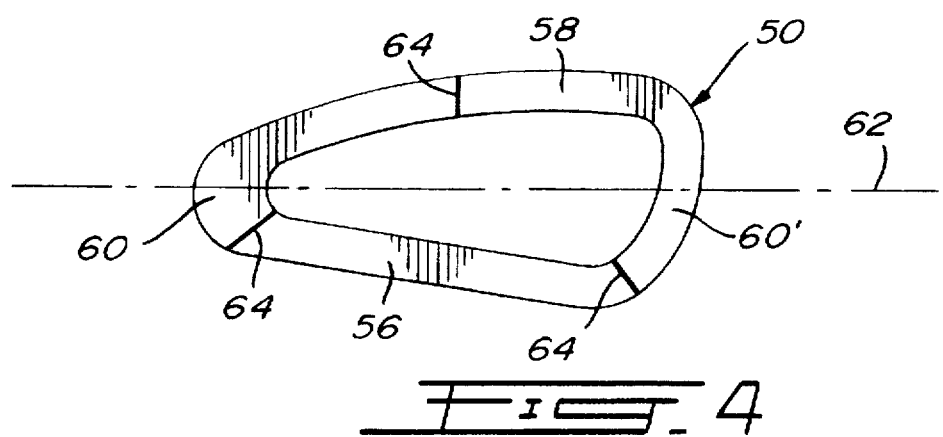
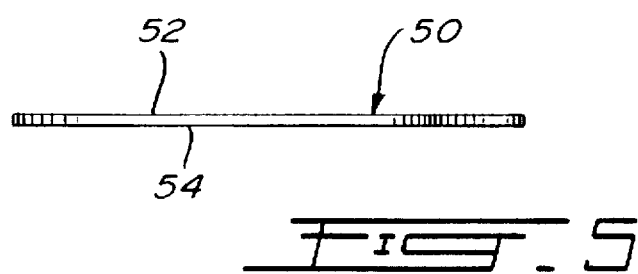
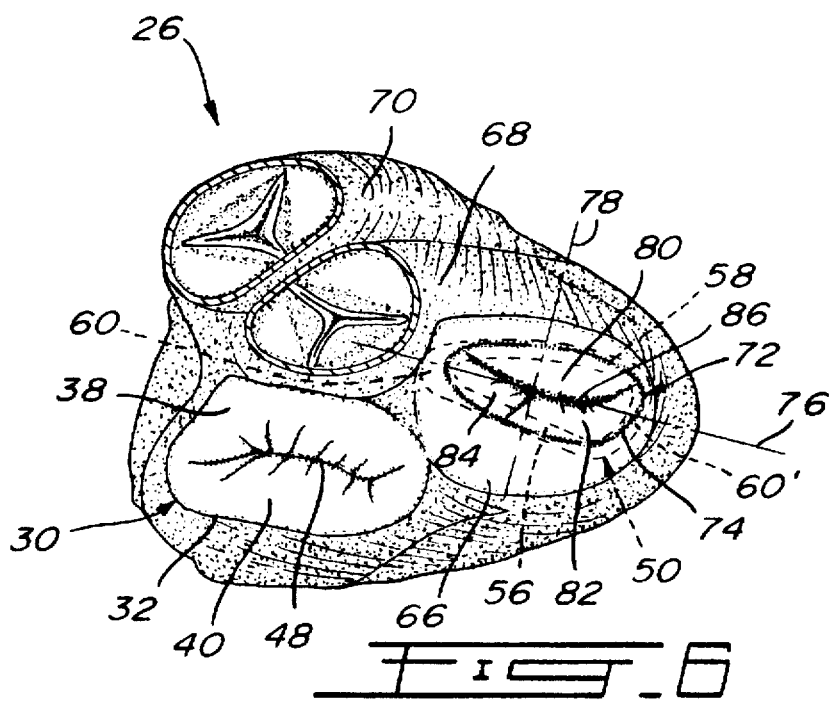

CARDIAC VALVULAR SUPPORT PROSTHESIS

BACKGROUND OF THE INVENTION

The present invention relates to a prosthesis intended for the surgical correction of cardiac valvular diseases and, more particularly, for the annuloplasty of mitral and tricuspid valves.

Mitral and tricuspid valves are present at the left and right atrio-ventricular junctions, respectively, of the human heart. These valves open and close in response to pressure gradient during each cardiac cycle of relaxation and contraction. Their function is to prevent the blood from flowing into atria from ventricles.

These valves consist of leaflets, an annulus from which the leaflets stem and a complex consisting of chordea and papillary muscles. The papillary muscles originate from ventricular muscle mass and are attached to the free margins of the leaflets through chordea. The size of the leaflets is such that when the heart contracts, the resulting increased blood pressure within the ventricle cavity pushes the leaflets towards the atrial cavity. During this process, the free margins of the leaflets come in apposition to each other and close the atrialventricular passage. The chordea and papillary muscle complex holds them in this position throughout the state of increased intraventricular pressure and prevents the leaflets from bulging into and opening in the atrial cavity. One of the conditions in which the mitral or tricuspid valve can become functionally incompetent is when the annulus become dilated, generally as a result of acquired and/or degenerative diseases and disorders. Due to the increased diameter of the annulus, the tips of the valve cusps fail to meet each other during systolic contraction. This nonclosure of the valve allows the blood to enter into atria from ventricles and renders them incompetent.

There have been mainly two different approaches in annuloplasty, i.e., re-modeling and narrowing of the annulus. In remodeling annuloplasty, after excising the excess tissue, a rigid metallic ring of appropriate size is implanted in the annulus which restores the natural shape of the annulus and reduces its diameter to a level where the leaflet length becomes adequate enough to close the valve. Although this technique has been applied successfully for the last so many years, it has many pitfalls. Unlike the natural annulus, the ring is rigid and does not decrease in diameter during systolic contractions or increase in diameter during diastolic expansions. Because of its rigid nature, during systole, the ring bulges into the left ventricular outflow tract, causing a systolic anterior motion (SAM), a well recognized and documented complication and thus giving rise to obstruction to the blood flow. The rigid ring does not allow the annulus to respond to the heamodynamic and functional changes produced within the heart under different physiological and pathological conditions. The annulus is unable to contract and dilate. Consequently, the sutures undergo stress and there is increased risk of ring dehiscence.

In narrowing annuloplasty, a flexible pursestring type of assembly is implanted at the annulus. The annulus is made narrow by adjusting the length of the string. In this type of repair, the natural shape and configuration of the valve is lost leading to curling of the leaflets and resulting in less than perfect repair and valve function. Since the string used is non-stretchable, the annulus does not dilate in high cardiac output states. The SAM problem is not seen in this type of repair provided excess tissue on posterior mitral cusp is excised.

Recently, a semi-rigid annuloplasty ring has been introduced. This ring is made of alternating strips of metal and plastic and covered with fabric. This configuration allows a certain amount of flexibility in antero-posterior direction. The natural shape of the valve is restored but the annulus is still unable to adjust to high output blood flow conditions and there is no increase in size as the age of the patient progresses.

SUMMARY OF THE INVENTION

It is therefore an object of the present invention to overcome the above drawbacks and to provide an improved support prosthesis which enables the annulus to dilate in response to heamodynamic and functional changes, increased blood flow and pressure, without affecting the operativeness of the leaflets.

In accordance with the present invention, there is provided a support prosthesis for a natural human heart valve having an annulus of generally oval configuration with a major axis and a minor axis and at least two leaflets stemming from said annulus and each moving along a naturally preordained path during systolic contraction or diastolic expansion. The support prosthesis of the invention consists of an oblong, annular flexible member of a size and shape to fit against the annulus, the member having a longitudinal axis and being made of a biocompatible material exhibiting elasticity only along the longitudinal axis so as to permit dilatation of the annulus along the major axis thereof, in response to heamodynamic and functional changes, while preventing dilatation of the annulus along the minor axis thereof so that the path along which each leaflet travels remains unaltered.

According to a preferred embodiment, the biocompatible material is a fibrous biocompatible material having fibers oriented in a manner to provide the aforesaid elasticity. Preferably, such a fibrous biocompatible material facilitates growth of endothelial cells so that the member becomes embedded in endothelium, thereby preventing clot formation; possible dehiscence of the member is completely eliminated. An example of a suitable material exhibiting these properties is a modified form of polytetrafluoroethylene sold under the trademark GORE-TEX. Suture stitches can pass through such a material so that no track or recesses are left behind, which can become sites for harboring infectious agents. This material also allows one to produce a seamless and jointless member, by either stamping or by simply cutting the member out in the desired shapes and sizes. The shapes are different for mitral and tricuspid valves. The member is made in different sizes in order to meet the clinical requirements in different individuals requiring different cardiac output.

Since the member is made of a single material, there is no possibility of material wear as seen with other support prosthesis made of several materials and having coverings.

According to another preferred embodiment, the member is substantially flat and has two opposite planar surfaces, thereby occupying minimal intracardiac space and volume. At least one of the surfaces is provided with orientation markers allowing the surgeon to orient the member while it is being placed in position.

Because of its pliable and flexible nature, the support prosthesis of the invention does not produce a systolic anterior motion of the mitral or tricuspid valve and it conforms to the seat of implantation and adjoining structures; in particular, the support prosthesis of the invention adapts to the shape of the aortic root and allows it to expand freely in response to heamodynamic and functional changes within the aorta. Complete flexibility allows natural contractibility of the annulus during systole and eliminates stress on the sutures and dehiscence of the member. The support prosthesis of the invention does not interfere with the normal dynamic motion of the mitral and tricuspid annulus during systole contraction or diastolic expansion. The use of such a support prosthesis prevents dilatation of the annulus along its minor axis and thereby prevents non-closure of the mitral and tricuspid valves during systolic contraction. During diastolic expansion, the annulus can dilate along its major axis in response to the heamodynamic and functional changes in different physiological and pathological states, while adequate support is provided by the prosthesis to the annulus. The support prosthesis according to the invention restores and retains the physiological size and shape of the annulus without rendering it stiff.

BRIEF DESCRIPTION OF THE DRAWINGS

Further features and advantages of the invention will become more readily apparent from the following description of preferred embodiments as illustrated by way of example in the accompanying drawings, in which:

FIG. 4 is a top plan view of a support prosthesis for a tricuspid valve, according to a preferred embodiment of the invention;

FIG. 5 is an elevational view thereof; and

FIG. 6 is a schematic sectional view of a natural human heart illustrating the tricuspid valve fitted with the support prosthesis of FIG. 4 shown in broken lines.

DESCRIPTION OF PREFERRED EMBODIMENTS

Figure 1:
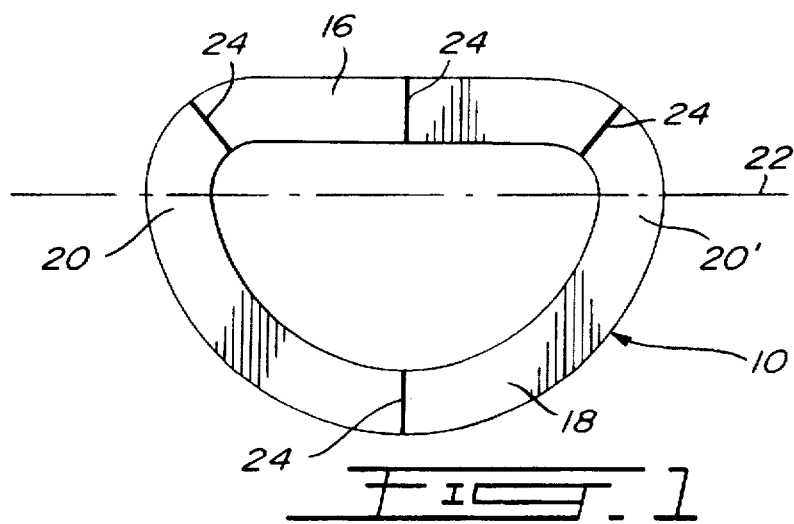
FIG. 1 is a top plan view of a support prosthesis for a mitral valve, according to a preferred embodiment of the invention.
Figure 2:
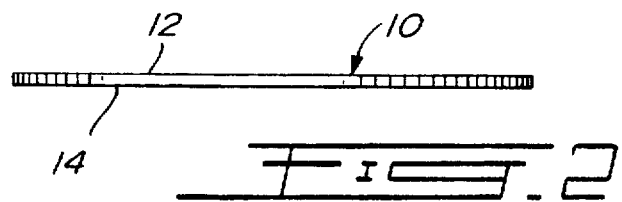
FIG. 2 is an elevational view thereof.
Figure 3:
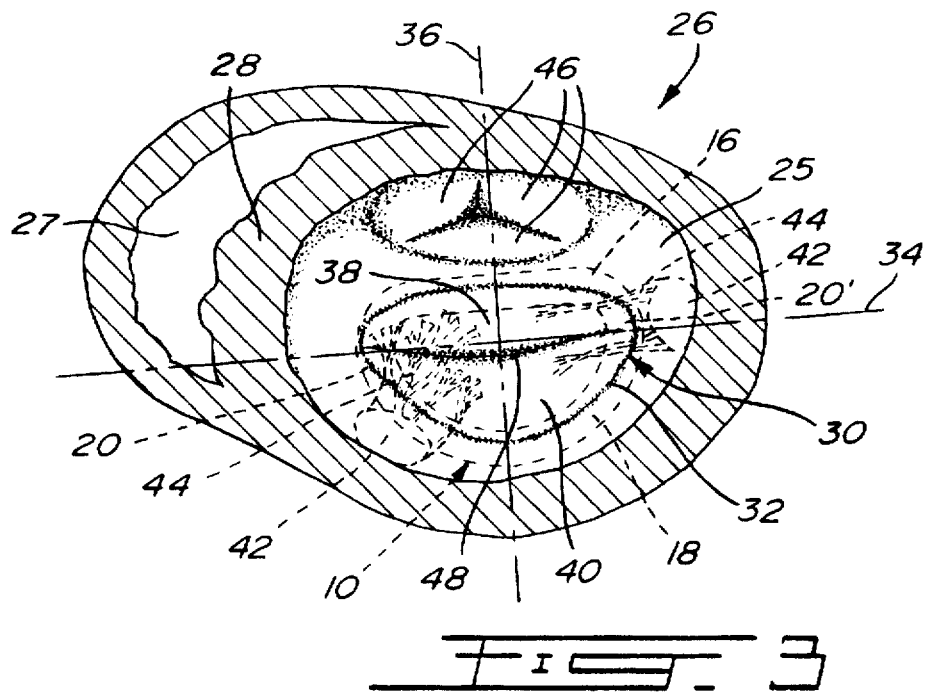
FIG. 3 is a schematic sectional view of a natural human heart illustrating the mitral valve fitted with the support prosthesis of FIG. 1 shown in broken lines.

The mitral prosthesis illustrated in FIGS. 1–3 consists of a substantially flat, oblong, annular member 10 having two opposite planar surfaces 12 and 14. The member 10 which is seamless and jointless comprises a rectilinear segment 16, a curved segment 18 and two end portions 20,20'. It is made of a fibrous biocompatible material which is flexible and has fibers oriented in a manner such as to provide elasticity only along the longitudinal axis 22. Due to such an elasticity, the end portions 20,20' are extensible along the axis 22 whereas the segments 16 and 18 remain in a fixed position relative to another. Both surfaces 12 and 14 are provided with orientation markers 24 allowing the surgeon to orient the member 10 while it is being placed in position against the annulus of a mitral valve.

FIG. 3 illustrates the left atrium 25 (only the bottom shown) of a normal human heart 26, which is separated from the right ventricle 27 by the ventricular septum 28. Disposed at the bottom of the left atrium 25 is the mitral valve 30 which comprises an annulus 32 of generally oval configuration with a major axis 34 and a minor axis 36, anterior and posterior leaflets 38,40 stemming from the annulus 32 and papillary muscles 42 attached to the free margins of the leaflets 38,40 through chordea 44. Also shown are the aortic cusps 46. The mitral prosthesis 10 has a size and shape to fit against the annulus 32. As shown, the rectilinear segment 16 of the prosthesis extends along a major portion of the annulus 32 from which stems the anterior leaflet 38, the curved segment 18 extending along a major portion of the annulus 32 from which stems the posterior leaflet 40. The mitral prosthesis 10 is secured to the annulus 32 by either continuous mattress suturing or by interrupted sutures, depending upon the discretion of the surgeon.

Since the end portions 20,20' of the mitral prosthesis 10 are extensible along the longitudinal axis 22 coincident with the major axis 34 of the annulus 32, the prosthesis 10 permits the annulus 32 to dilate along its major axis 34 in response to the increased blood flow and pressure in different physiological and pathological states, thereby enabling the valve opening 48 to increase in length so as to accommodate such an increased blood flow. On the other hand, since the segments 16 and 18 of the mitral prosthesis 10 remain in a fixed position relative to one another, the prosthesis 10 prevents the annulus 32 from dilating along its minor axis 36 so that prevents the paths along which the leaflets 38,40 travel remain unaltered. The full operativeness of the anterior leaflet 38 and posterior leaflet 40 is thus retained during increased blood flow and pressure.

The tricuspid prosthesis illustrated in FIGS. 4–6 also consists of a substantially flat, annular member 50 having two opposite planar surfaces 52 and 54. The member 50 which is seamless and jointless comprises a rectilinear segment 56, a slightly curved segment 58 and two end portions 60,60'. Similarly to member 10, the member 50 is made of a fibrous biocompatible material which is flexible and has fibers oriented in a manner such as to provide elasticity only along the longitudinal axis 62. Due to such an elasticity, the end portions 60,60' are extensible along the axis 62 whereas the segments 56 and 58 remain in a fixed position relative to one another. Both surfaces 52 and 54 are provided with orientation markers 64 allowing the surgeon to orient the member 50 while it is being placed in position against the annulus of a tricuspid valve.

FIG. 6 illustrates the base of the ventricular part of the heart 26 with the atria and great vessels removed. Reference numerals 66, 68 and 70 designate the right atrium (only the bottom shown), aorta and right ventricle, respectively. Disposed at the bottom of the right atrium 66 is the tricuspid valve 72 which comprises an annulus 74 of generally oval configuration with a major axis 76 and a minor axis 78, and anterior, posterior and septal leaflets 80,82,84 stemming from the annulus 74; the papillary muscles and chordea which attach the papillary muscles to the free margins of the leaflets 80,82 and 84 are not shown. The tricuspid prosthesis 50 has a size and shape to fit against the annulus 74. As shown, the rectilinear segment 56 of the prosthesis extends along a major portion of the annulus 74 from which stem the posterior and septal leaflets 82,84, the curved segment 58 extending along a major portion of the annulus 74 from which stems the anterior leaflet 80. The tricuspid prosthesis is secured to the annulus 74 by either continuous mattress suturing or by interrupted sutures, depending upon the discretion of the surgeon.

Since the end portions 60,60' of the tricuspid prosthesis 50 are extensible along the longitudinal axis 62 coincident with the major axis 76 of the annulus 74, the prosthesis 50 permits the annulus 74 to dilate along its major axis 76 in response to the increased blood flow and pressure in different physiological and pathological states, thereby enabling the valve opening 86 to increase in length so as to accommodate such an increased blood flow. On the other hand, since the segments 56 and 58 of the tricuspid prosthesis 50 remain in a fixed position relation to one another, the prosthesis 50 prevents the annulus 74 from dilating along its minor axis 78 and so that the paths along which the leaflets 80,82,84 travel remain unaltered. The full operativeness of the anterior leaflet 80, posterior leaflet 82 and septal leaflet 84 is thus retained during increased blood flow and pressure.

I claim:

1. A support prosthesis for a natural human heart valve having an annulus of generally oval configuration with a major axis and a minor axis and at least two leaflets stemming from said annulus and each moving along a naturally preordained path during systolic contraction or diastolic expansion, said support prosthesis consisting of an oblong, annular flexible member of a size and shape to fit against said annulus, said member having a longitudinal axis and being made of a biocompatible material exhibiting elasticity only along said longitudinal axis so as to permit dilatation of said annulus along the major axis thereof, in response to hemodynamic and functional changes, while preventing dilatation of said annulus along the minor axis thereof so that the path along which each said leaflet travels remains unaltered.

2. A support prosthesis as claimed in claim 1, wherein said biocompatible material is a fibrous material having fibers oriented in a manner to provide said elasticity.

3. A support prosthesis as claimed in claim 2, wherein said fibrous biocompatible material facilitates growth of endothelial cells so that said member becomes embedded in endothelium, thereby preventing clot formation.

4. A support prosthesis as claimed in claim 3, wherein said fibrous biocompatible material is a modified form of polytetrafluoroethylene sold under the trademark GORE-TEX.

5. A support prosthesis as claimed in claim 1, wherein said member is seamless and jointless.

6. A support prosthesis as claimed in claim 1, wherein said member is substantially flat and has two opposite planar surfaces, and wherein at least one of said surfaces is provided with orientation markers.

7. A support prosthesis as claimed in claim 1, wherein said member has a size and shape to fit against the annulus of a mitral valve.

8. A support prosthesis as claimed in claim 7, wherein the leaflets of said mitral valve comprise anterior and posterior leaflets and wherein said member has a rectilinear segment corresponding to said anterior leaflet and a curved segment corresponding to said posterior leaflet.

9. A support prosthesis as claimed in claim 1, wherein said member has a size and shape to fit against the annulus of a tricuspid valve.

10. A support prosthesis as claimed in claim 9, wherein the leaflets of said tricuspid valve comprise septal, anterior and posterior leaflets and wherein said member has a rectilinear segment corresponding to said posterior and septal leaflets and a curved segment corresponding to said anterior leaflet.

* * * * *